United States Patent
Gillespie et al.

(10) Patent No.: US 7,957,817 B1
(45) Date of Patent: Jun. 7, 2011

(54) MEDICAL ELECTRODE AND TOOL FOR DELIVERING THE ELECTRODE

(75) Inventors: Walter D. Gillespie, San Diego, CA (US); David G. Matsuura, Encinitas, CA (US); Gary R. Dulak, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 125 days.

(21) Appl. No.: 11/849,564

(22) Filed: Sep. 4, 2007

(51) Int. Cl.
*A61N 1/00* (2006.01)

(52) U.S. Cl. .................................................... 607/116
(58) Field of Classification Search .................. 607/115, 607/116, 117, 118, 126, 127, 128, 130; 81/177.7–177.75
See application file for complete search history.

(56) References Cited

U.S. PATENT DOCUMENTS

| | | | | |
|---|---|---|---|---|
| 1,398,234 | A | * | 11/1921 | Landis ............................ 81/450 |
| 1,628,553 | A | * | 5/1927 | Owens ............................ 81/436 |
| 5,095,905 | A | * | 3/1992 | Klepinski ....................... 600/377 |
| 6,058,813 | A | * | 5/2000 | Bryant et al. ................. 81/176.15 |
| 6,093,197 | A | * | 7/2000 | Bakula et al. .................. 606/129 |
| 6,600,956 | B2 | * | 7/2003 | Maschino et al. ............. 607/118 |
| 6,918,908 | B2 | | 7/2005 | Bonner et al. |
| 7,020,531 | B1 | | 3/2006 | Colliou et al. |
| 7,544,197 | B2 | * | 6/2009 | Kelsch et al. .................. 606/129 |
| 2004/0243211 | A1 | | 12/2004 | Colliou et al. |
| 2006/0030919 | A1 | | 2/2006 | Mrva et al. |
| 2006/0047289 | A1 | | 3/2006 | Fogel |
| 2006/0089690 | A1 | | 4/2006 | Gerber |
| 2007/0021736 | A1 | | 1/2007 | Johnson |

FOREIGN PATENT DOCUMENTS

WO WO 02/087657 A2 11/2002
WO WO 02/087657 A3 11/2002

* cited by examiner

*Primary Examiner* — Mark W Bockelman
*Assistant Examiner* — Elizabeth K So

(57) ABSTRACT

Disclosed herein is a tool for delivering an implantable electrode about a body structure of a patient. In one embodiment, the tool includes a shaft and an electrode tray. The shaft includes a proximal end and a distal end. The electrode tray is articulatably coupled to the distal end and configured to maintain the electrode in an open configuration until the electrode is delivered about the body structure.

11 Claims, 12 Drawing Sheets

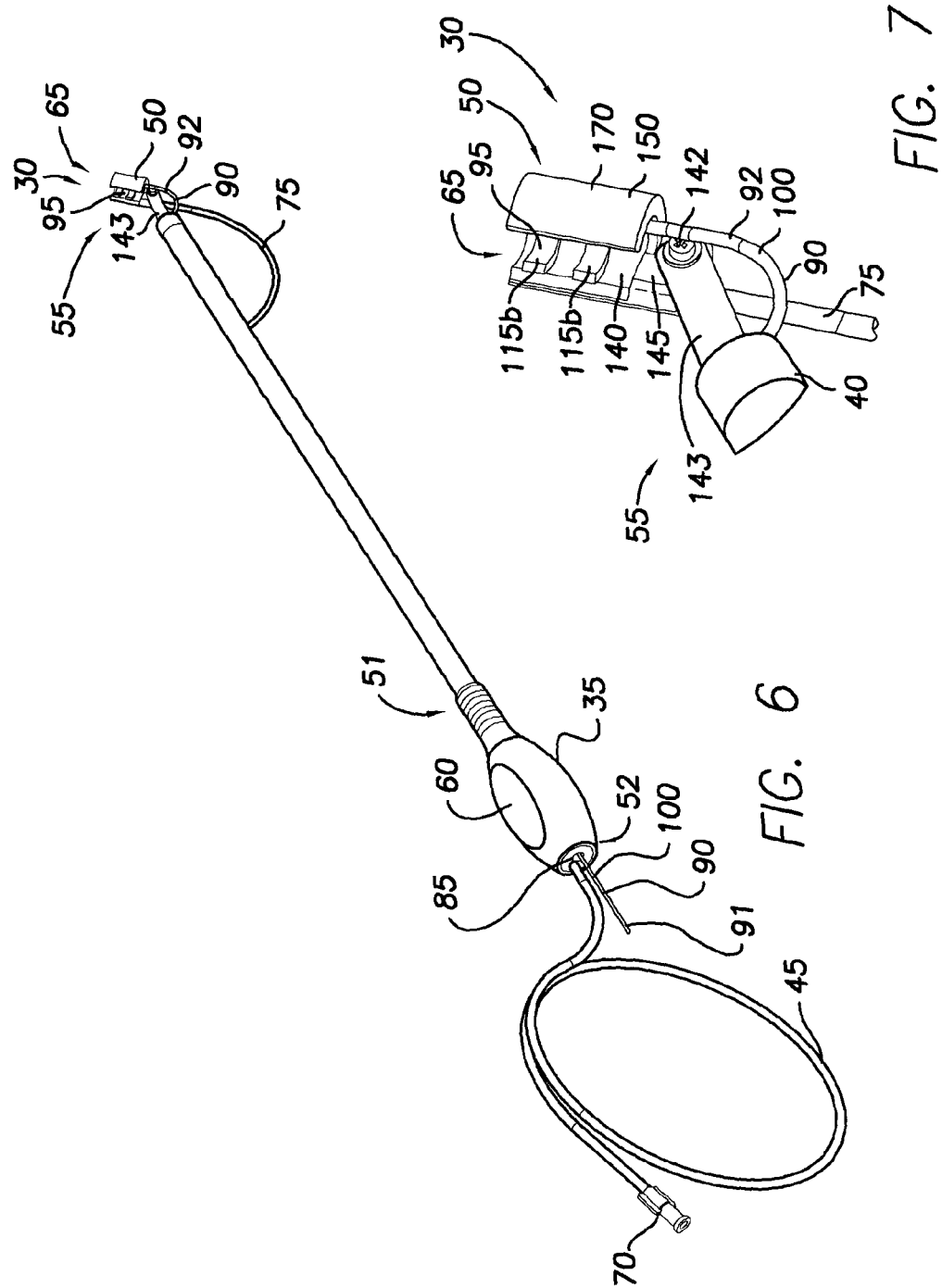

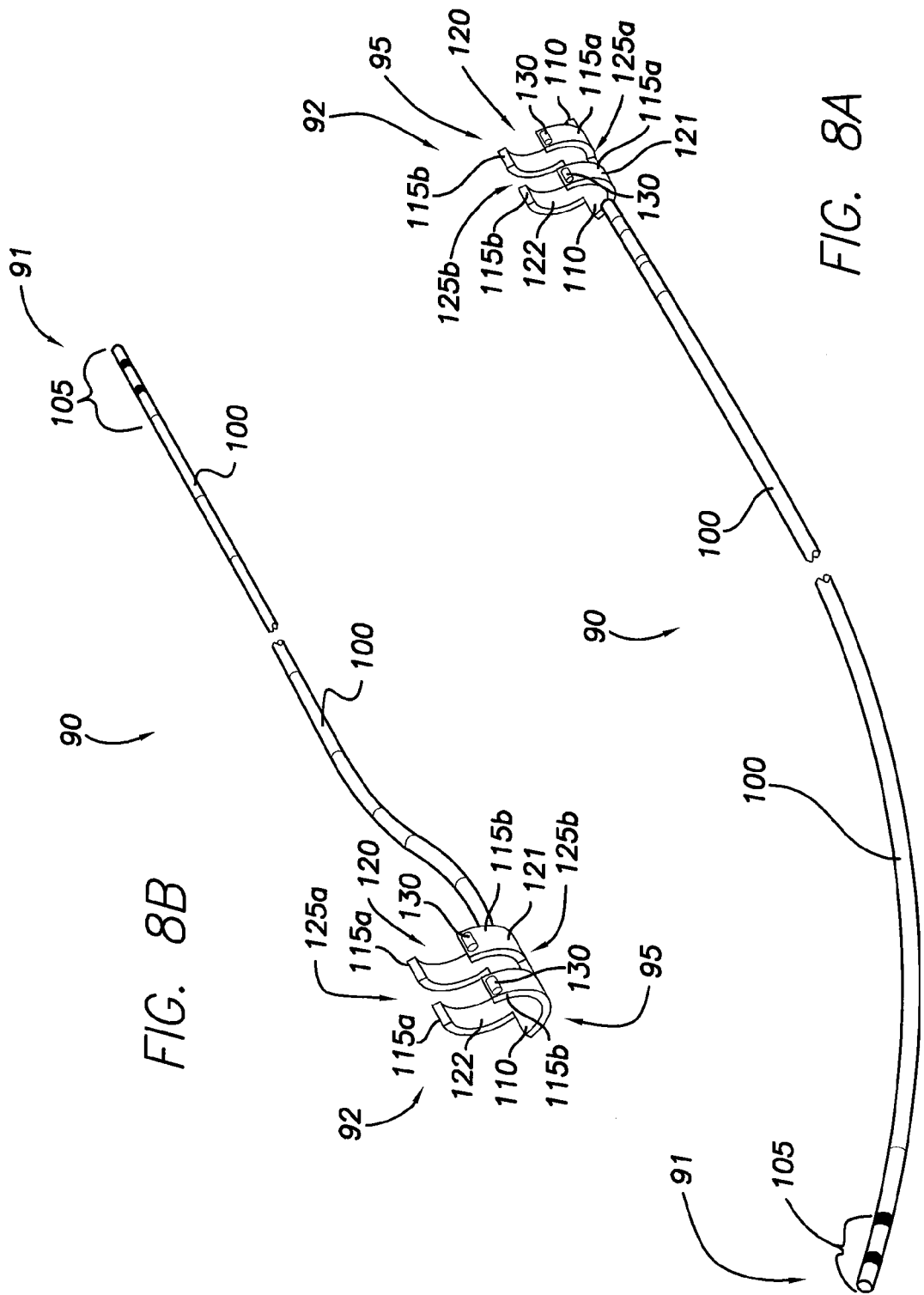

MEDICAL ELECTRODE AND TOOL FOR DELIVERING THE ELECTRODE

FIELD OF THE INVENTION

The present invention relates to methods and apparatus for the delivery and implantation of an implantable medical lead within an animal or human. More specifically, the present invention relates to methods and apparatus for the delivery and attachment of an electrode of an implantable medical lead to an anatomical structure of an animal or human.

BACKGROUND OF THE INVENTION

Many medical disorders can be treated by the attachment of an electrode of an implantable medical lead to a body structure, such as a nerve or nerve bundle. Such electrodes can provide therapeutic electrical stimulation to the body structure and/or take direct measurement of local electrical activity.

Attaching an electrode to a fragile body structure such as a nerve or nerve bundle is difficult and presents significant risks of damage to the body structure.

There is a need in the art for an electrode and electrode delivery tool that reduces the difficulty and risk associated with attaching an electrode to a fragile body structure. There is also a need in the art for a method of attaching an electrode to a fragile body structure, the method having a reduced level of difficulty and risk.

SUMMARY

Disclosed herein is a tool for delivering an implantable electrode about a body structure of a patient. In one embodiment, the tool includes a shaft and an electrode tray. The shaft includes a proximal end and a distal end. The electrode tray is articulatably coupled to the distal end and configured to maintain the electrode in an open configuration until the electrode is delivered about the body structure.

Disclosed herein is a medical system for administering electrotherapy to a body structure. In one embodiment the system includes a lead and a tool. The lead includes a longitudinally extending body and an electrode coupled to a distal end of the body. The electrode includes a generally cylindrical body having a gap defined therein when the electrode is in an open configuration. The tool is for delivering the electrode about the body and includes a shaft and a tray articulatably coupled to a distal end of the shaft. The tray is generally cylindrical and includes a gap defined therein. The electrode gap and tray gap align to allow the body structure to enter the electrode when the electrode is held in an open configuration within the tray.

Disclosed herein is an implantable electrode for attachment to a body structure. In one embodiment, the electrode includes a spine, a first pair of spaced apart ribs extending from a first side of the spine, and a second pair of spaced apart ribs extending from a second side of the spine. The first and second pair of ribs oppose each other and are staggered relative to each other such that the ribs of the first pair mesh in alternating fashion with the ribs of the second pair when the electrode is in a closed configuration.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 4 is an enlarged view of the distal end of the tool as depicted in FIG. 3.

FIG. 6 is a view similar to that depicted in FIG. 1, except the distal end of the tool is in a deflected state.

FIG. 7 is an enlarged view of the distal end of the tool as depicted in FIG. 6.

FIGS. 8A and 8B are a distal isometric view of the lead with its electrode in an open state.

DETAILED DESCRIPTION

Disclosed herein is a delivery tool 10 for, and method of, delivering and attaching an electrode of an implantable medical lead to a structure in the body of an animal or human. In one embodiment, the delivery tool 10 is used to place the electrode in circumferential contact with a nerve bundle or other similar body structure. The delivery tool 10 is then removed, leaving the electrode attached to the nerve bundle.

Figure 1:
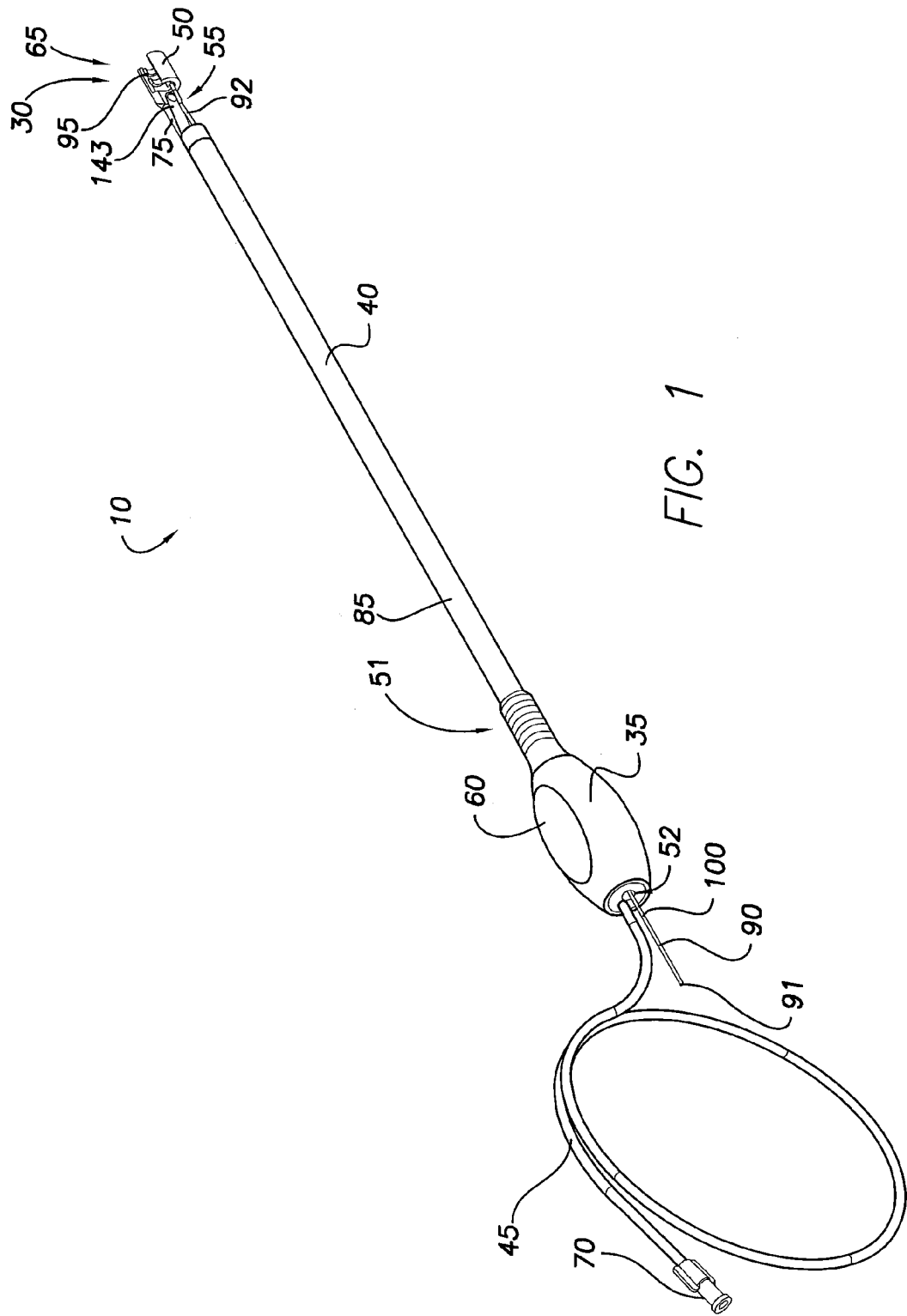
FIG. 1 is a rear isometric view of the tool.
Figure 2:
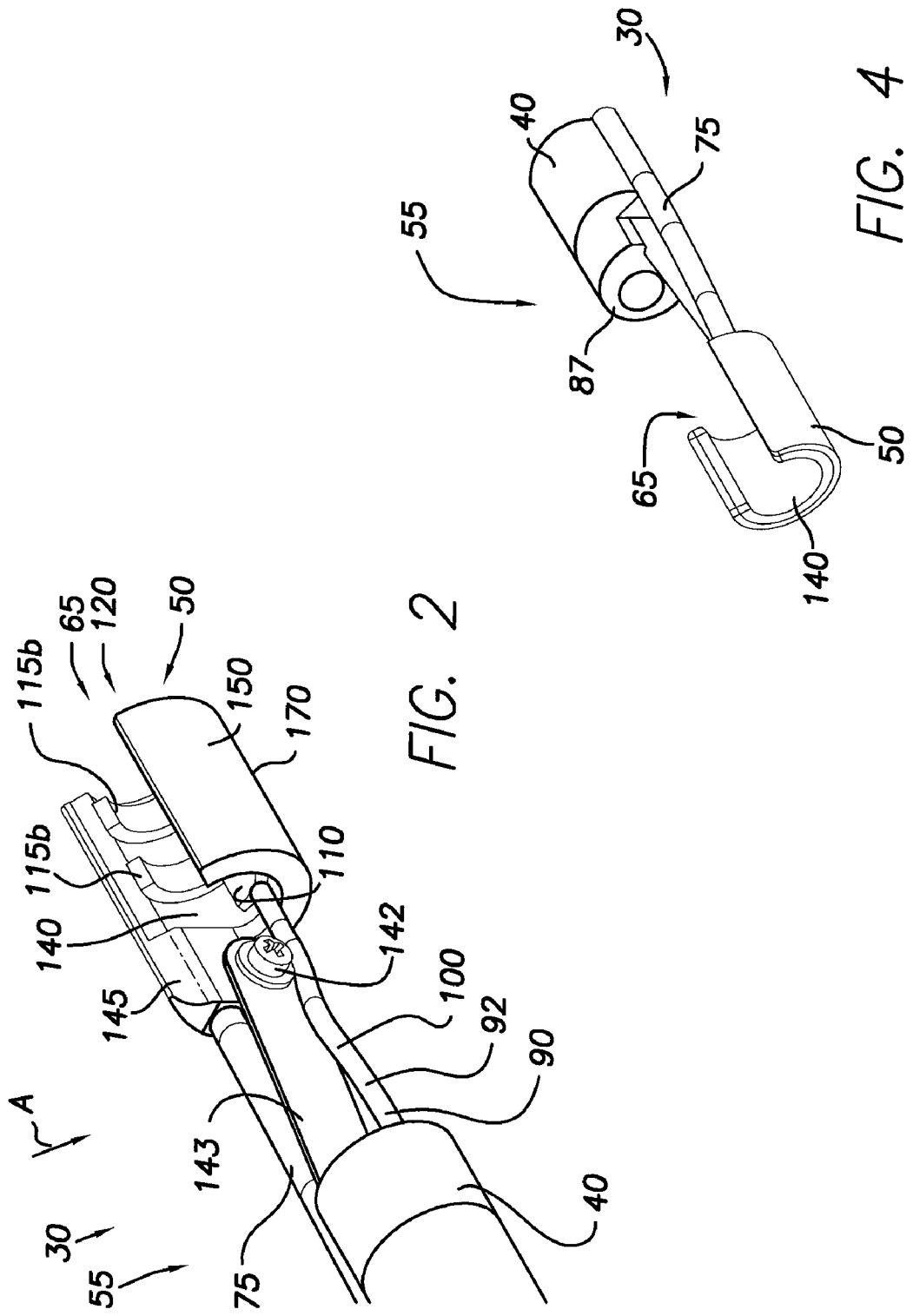
FIG. 2 is an enlarged view of the distal end of the tool as depicted in FIG. 1.
Figure 3:
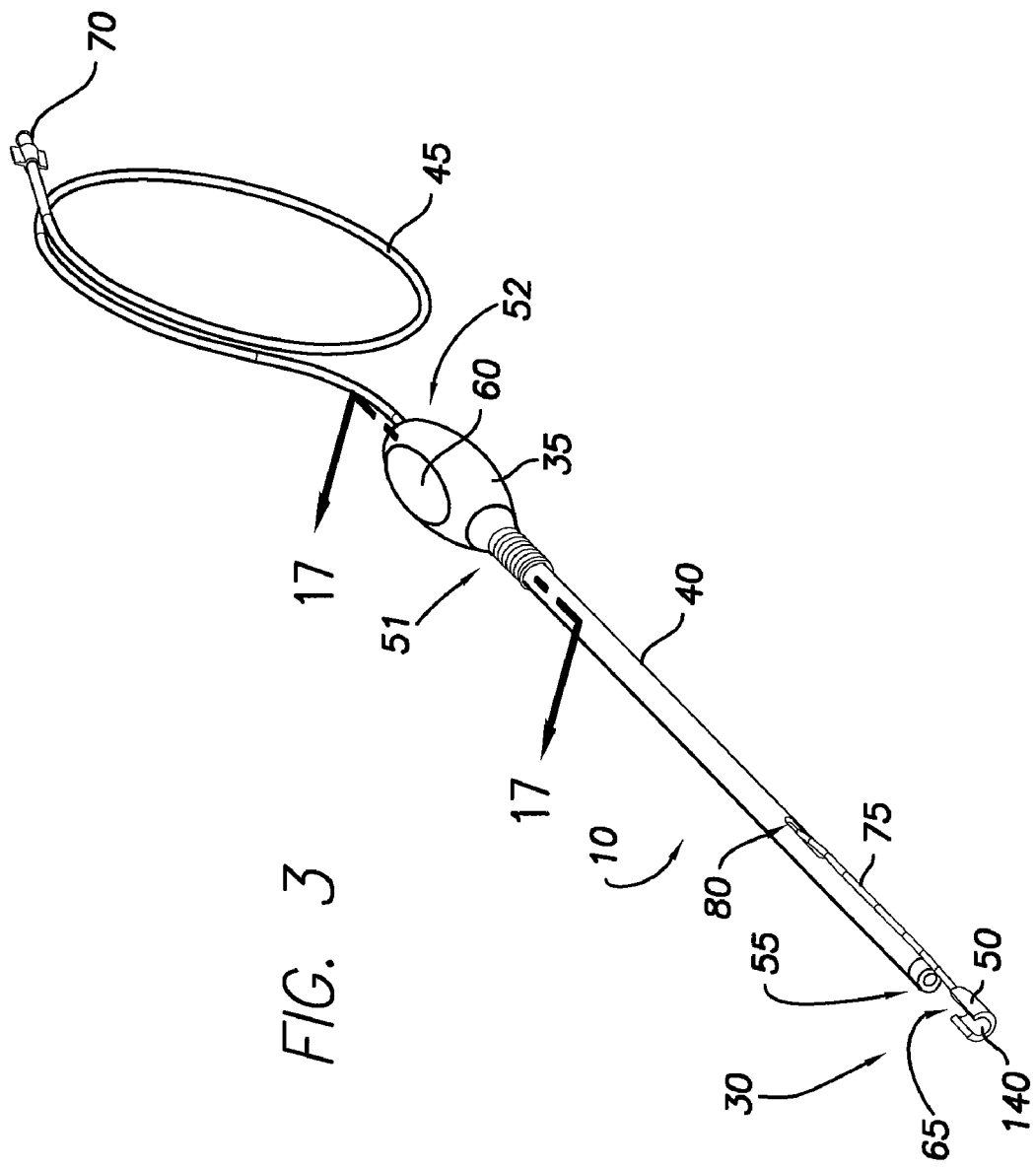
FIG. 3 is a front isometric view of the tool.
Figure 5:
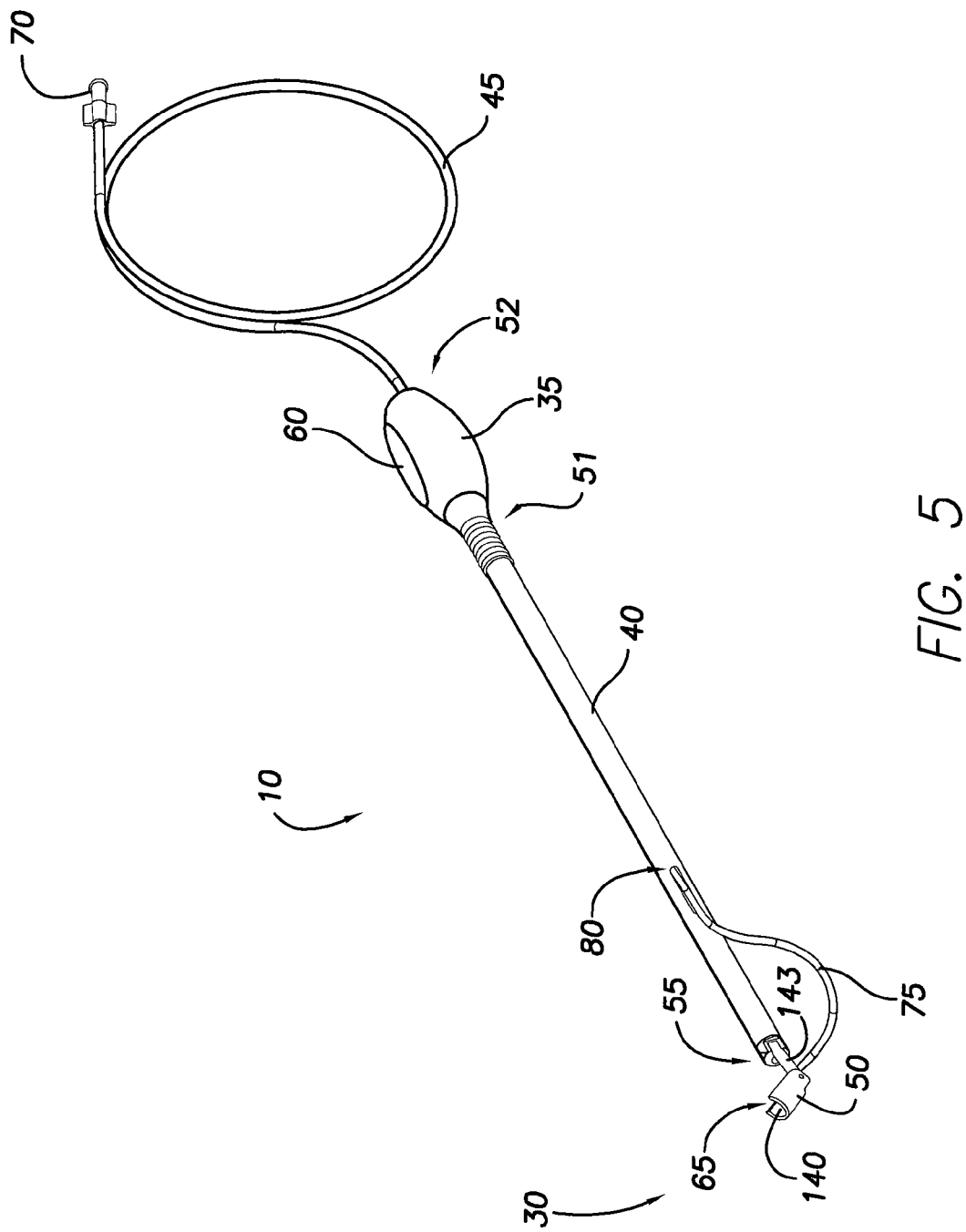
FIG. 5 is a view similar to that depicted in FIG. 3, except the distal end of the tool is in a deflected state.

For a discussion of the overall configuration of the tool 10, reference is made to FIGS. 1-7. FIG. 1 is a rear isometric view of the tool 10. FIG. 2 is an enlarged view of the distal end 30 of the tool 10 as depicted in FIG. 1. FIG. 3 is a front isometric view of the tool 10. FIG. 4 is an enlarged view of the distal end 30 of the tool 10 as depicted in FIG. 3. FIG. 5 is a view similar to that depicted in FIG. 3, except the distal end 30 of the tool 10 is in a deflected state. FIG. 6 is a view similar to that depicted in FIG. 1, except the distal end 30 of the tool 10 is in a deflected state. FIG. 7 is an enlarged view of the distal end 30 of the tool 10 as depicted in FIG. 7.

As illustrated in FIGS. 1, 3, 5 and 6, in one embodiment, the tool 10 includes a handle 35, a tubular body or shaft 40, an air/vacuum line 45, and an electrode capture or retention tray 50. The handle 35 is mounted on a proximal end 52 of the shaft 40, which extends distally from the handle 35. The air/vacuum line 45 extends proximally from the shaft proximal end 52. As can be understood from FIGS. 1-7, in one embodiment, the tray 50 is pivotally coupled to a distal end 55 of the shaft 40.

As indicated in FIGS. 1, 3, 5 and 6, in one embodiment, the handle 35 is bulb-shaped with a flattened region 60, and the tray 50 is generally cylindrically shaped with a slot 65 longitudinally extending through a side of the tray 50. In one embodiment, the slot 65 and flattened region 60 are generally aligned with each other to indicate to a physician using the tool 10 the orientation of the tray 50 when the tool distal end 30 is located within a patient during an implantation procedure. In one embodiment, the handle 35 includes a multiplicity of annular grooves 51 near the distal extent of the handle 35 to give the user additional longitudinal grip.

As depicted in FIGS. 1 and 6, the air/vacuum line 45 is connected to the shaft distal end 52. In one embodiment, the connection between the line 45 and the shaft distal end 52 is permanent. In one embodiment, the line 45 terminates at its proximal end with a female luer 70, thereby allowing the line to be securely connected to a vacuum or air source.

As shown in FIGS. 3-7, a distal air/vacuum line 75 extends from an opening 80 in the outer circumferential wall of the shaft 40 proximal of the shaft distal end 55. The distal air/vacuum line 75 is in fluid communication with the proximal air/vacuum line 45. In one embodiment as indicated in later discussed FIG. 17, the lines 45, 75 are individual pieces fluidly coupled to each other via a fluid/vacuum chamber 200 defined in the handle 35. In one embodiment, the lines 45, 75 are simply proximal and distal portions of a continuous air/vacuum line longitudinally routed though the shaft 40. The air/vacuum lines 45, 75 fluidly couple the electrode retention tray 50 to the air/vacuum source coupled to the luer 70.

As can be understood from FIGS. 1, 3, 4 and 6, a lead receiving lumen longitudinally extends through the shaft 40 and daylights at the shaft proximal and distal ends 52, 55 as proximal and distal lead port 85, 87. As shown in FIGS. 1, 2, 6 and 7, when a lead 90 is located within the lead receiving lumen, a proximal end 91 of the lead 90 will extend from the proximal port 85, and a distal end 92 of the lead 90 will extend from the distal port 87.

In one embodiment, the shaft 40 is made of a biocompatible metal or rigid plastic such as stainless steel or polycarbonate, etc. The handle 35 may be made of polycarbonate, etc. The air/vacuum line 45, 75 may be made of polyethylene or some other common flexible tubing that is biocompatible. The lead receiving lumen 85, 87 may be made of polycarbonate or Ultem, etc. In one embodiment, the shaft 40 is molded, extruded or otherwise formed via a thermoforming process. The line 45, 47 and/or lumen 85, 87 are defined in the shaft 40 during the process, or the shaft 40 is formed about the line 45, 47 and/or lumen 85, 87 during the process. Subsequent to the formation of the shaft 40, the handle 35 is formed about the shaft 40 via an injection molding process.

In one embodiment, the shaft 40 has an outer diameter of between approximately 0.15" and approximately 0.25". In one embodiment, the lead receiving lumen 85, 87 has an inner diameter of between approximately 0.05" and approximately 0.2". In one embodiment, the lumen of the air/vacuum line 45, 75 has a diameter of between approximately 0.025" and approximately 0.1".

For a discussion of an embodiment of a lead 90 for use with the tool 10 described herein, reference is made to FIGS. 8A and 8B, which are distal isometric views of the lead 90 with its electrode 95 in an open state. As shown in FIGS. 8A and 8B, the lead 90 includes proximal and distal ends 91, 92, an electrode 95, a lead body 100 with a cable conductor extending there through or a conductor cable 100 that generally forms a lead body itself, and a connective end 105. The electrode 95 is located at the distal end 92, and the connective end 105 is located at the proximal end 91. In one embodiment, the connective end 105 is adapted to electrically couple with a pulse generator such as a pacemaker, defibrillator, implantable cardioverter defibrillator ("ICD"), etc. The conductor cable 100 extends between and electrically couples the electrode 95 and connective end 105.

In one embodiment, the body or conductor cable 100 is an electrically conductive core surrounded by an electrically insulating jacket. In one embodiment, the electrically conductive core is formed of a metal or alloy material such as platinum, platinum-iridium, stainless steel, etc., and the electrically insulating jacket is formed of PTFE, ETFE, polyimide or other common insulative materials. In one embodiment, the body or conductor cable 100 has a diameter of between approximately 0.002" and approximately 0.007".

As depicted in FIGS. 8A and 8B, in one embodiment, the electrode 95 is generally cylindrical and includes an arcuate spine 110 and pairs of spaced-apart arcuate ribs 115a and 115b transversely extending from each side of the spine 110. As shown in FIGS. 8A and 8B, when the electrode 95 is in an open state, a longitudinally extending slot or opening 120 is defined between the free ends of the ribs 115a and 115b to extend from the outer circumferential surface 121 of the electrode 95 to the inner circumferential surface 122 of the electrode 95. The opening 120 allows a body structure 25 such as a nerve bundle 25 to enter into the space defined by inner circumferential surface 122 of the electrode capture/retention tray 50.

As indicated in FIGS. 8A and 8B, in one embodiment, each side of the electrode 95, or more specifically the spine 110, will have two ribs 115 spaced-apart or separated by a gap 125a and 125b. However, in other embodiments, each side of the electrode 95 will have a greater or lesser number of ribs 115 and gaps 125a and 125b.

Figure 16:
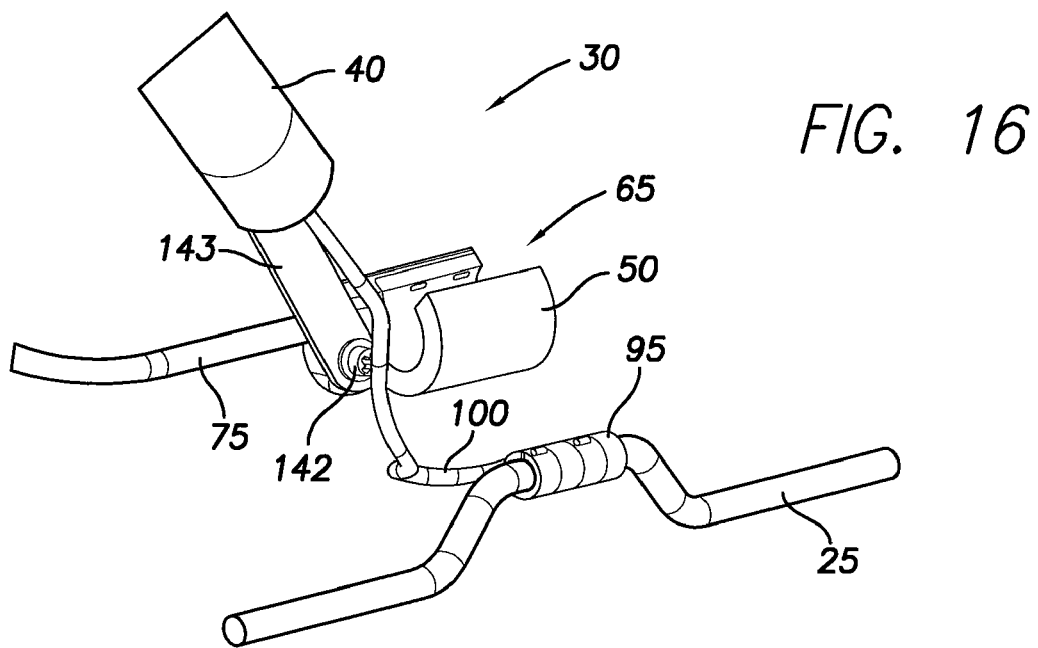
FIG. 16 is the same view depicted in FIG. 15, except the electrode is engaged about the nerve bundle and the electrode has been released from the tray.

As illustrated in FIGS. 8A and 8B, in one embodiment, the first side's spaced-apart ribs 115a are longitudinally offset from the second side's spaced-apart ribs 115b. As a result and as indicated in FIG. 16 discussed later in this Detailed Discussion, when the electrode 95 is in a closed state to encircle or enclose a body structure 25 such as a nerve bundle 25, the offset relationship between the ribs 115 of the two sides allows the first side ribs 115a to be received between the gaps 125b separating the second side ribs 115b and the second side ribs 115b to be received between the gaps 125a separating the first side ribs 115a.

In one embodiment, one or more ribs 115 will extend from a single side of the electrode 95, or more specifically the spine 110. In such an embodiment, the one or more ribs 115 may or may not be space-apart or separated from each other.

As indicated in FIGS. 8A and 8B, in one embodiment, one or more protrusions 130 project from the outer circumferential surface 121 of the ribs 115a, 115b. In one embodiment, the protrusions 130 are located near the free ends of the ribs 115a, 115b. In other embodiments, the protrusions 130 are located at other locations on the outer circumferential surface 121 of the ribs 115a, 115b. In one embodiment, one or more protrusions 130 are located on the outer circumferential surface 121 of the spine 110. As illustrated in later discussed FIGS. 11 and 12, the protrusions 130 are received in air/vacuum ports 135 in the inner circumferential surface 140 of the of the electrode retention tray 50 when the electrode 95 resides in the tray 50 as depicted FIGS. 1, 2, 6 and 7.

In one embodiment, the electrode 95 or at least a portion of the inner circumferential surface 122 is made of an electrically conductive metal or alloy such as platinum, platinum-iridium, stainless steel, etc. In one embodiment, where the cylindrical wall of the electrode 95 is a sandwich configuration having an insulating outer circumferential layer forming the outer circumferential layer 121 and an electrically conductive inner circumferential layer forming the inner circumferential layer 122, the outer insulating layer will be made of a material such as silicone, PTFE or other insulative polymers and the inner conductive layer will be formed of silicone, PTFE or other insulative polymers.

In one embodiment, the electrode 95 is molded or otherwise formed via a thermoforming process. In one embodiment, where the electrode 95 has the above-described sandwich configuration, the inner circumferential layer is formed via a molding process and then the outer circumferential layer is formed over the inner circumferential layer via an overmolding process. Alternatively, in one embodiment, the inner and outer circumferential layers forming the electrode 95 are formed via a co-extrusion process.

As can be understood from FIGS. 8A and 8B, in one embodiment, the inner cylindrical volume defined by the inner circumferential surface 122 has a diameter of between approximately 1 mm and approximately 7 mm when the electrode 95 is in a closed configuration as depicted in later discussed FIG. 16. In one embodiment, the inner cylindrical volume has a longitudinally extending length of between approximately 2 mm and approximately 20 mm. In one embodiment, the cylindrical wall of the electrode 95 has a radial thickness of between the inner and outer circumferential surfaces 121, 122 of between approximately 0.5 mm and approximately 4 mm. In one embodiment, the slot/opening 120 has a circumferentially extending width of between approximately 0.5 mm and approximately 8 mm when the electrode 95 is held in a fully open state as depicted in FIG. 2.

In FIGS. 8A and 8B, the electrode 95 is depicted in an open configuration. However, in one embodiment, the electrode 95 must be maintained in the open configuration by being held in tray 50 as illustrated in FIG. 2. In such an embodiment, the electrode 95 is biased to assume a closed configuration (as depicted in later discussed FIG. 16) when not maintained in an open configuration (as depicted in FIG. 2). Thus, when electrode 95 is released from the tray 50, the electrode biases to the closed configuration illustrated in FIG. 16.

As indicated in FIGS. 2 and 7, in one embodiment, the electrode tray 50 includes an arm 145 and a cylindrical portion 150. The arm 145 extends proximally from the cylindrical portion 150. A shaft arm 143 extends distally from the shaft distal end 55. A pin, screw or bolt 142 transversely extends through both the shaft arm 143 and the tray arm 145 to pivotally couple the tray 50 to the shaft arm 143.

As can be understood from a comparison of FIGS. 1-2 to FIGS. 5-7, the tray 50 can pivotally displace relative to the shaft distal end 55 and, more specifically, the shaft arm 143. To pivotally displace the tray 50, the lead cable conductor 100 is fed distally through the lead receiving lumen of the tool shaft 40 while the lead electrode 95 is securely received in the electrode tray 50. Because the lead cable conductor 100 intersects the combined electrode 95 and tray 50 at a location offset from the pivot axis created by the longitudinal axis of the bolt 142, the combined electrode 95 and tray 50 are caused to pivot about the bolt 142 from the straight forward orientation depicted in FIGS. 1-2 to the angled orientation depicted FIGS. 5-7.

In one embodiment, the force required to cause the tray 50 to pivot about the pivot axis 142 can be predetermined at the time of assembly by regulating the amount of torque used to tighten the bolt 142. The force required to cause the tray 50 to pivot about the pivot axis 142 can also be predetermined at the time of assembly by selecting a tube with a proper stiffness for the air/vacuum line 75 extending between the tray 50 and the shaft distal end 55.

As shown in FIGS. 5 and 6, the distal air/vacuum line 75 has sufficient slack such that the line 75 does not prevent the tray 50 from pivoting about the pivot axis 142. The slack and flexibility of the air/vacuum line 75 accommodates the articulation of the tray 50 to prevent kinking of the air/vacuum line 75 and to reduce the amount of effort required to articulate the tray 50. Similarly, the lead body 100 bends to accommodate the articulation of the tray 50 when the electrode 95 is held within the tray 50.

In one embodiment, the tray 50 is capable of being pivoted about the pivot axis 142 from an orientation generally axially aligned with a longitudinal axis of the tool shaft 40 (see FIGS. 1-2) to an orientation that is between approximately 45 degrees to approximately 90 from being aligned with the longitudinal axis of the tool shaft 40 (see FIGS. 5-7).

As can be understood from FIGS. 1 and 6, by grasping the lead proximal end 91 protruding from the proximal port 85 and displacing the lead 90 distally or proximally relative to the tool handle 35, the pivot angle of the tray 50 relative to the tool shaft distal end 55 can be adjusted to further increase the pivot or reduce the pivot.

While in one embodiment the tray 50 is pivotally coupled to the shaft distal end 55, other embodiments will employ other configurations for attaching the tray 50 to the shaft distal end 55 and allowing the tray 50 to displace relative to the shaft distal end 55. For example, as can be understood from FIGS. 2 and 7, in one embodiment, the shaft arm 143 is thin and flexible such that longitudinal displacement of the lead body 100 through the shaft 40 causes the tray 50 with the electrode 95 therein to articulate or otherwise displace relative to the shaft distal end 55. In another embodiment, the shaft arm 143 is thin an malleable, and the electrode tray 50 contacting a body structure can cause the tray 50 to deflect in any desired plane and angle.

Figure 9:
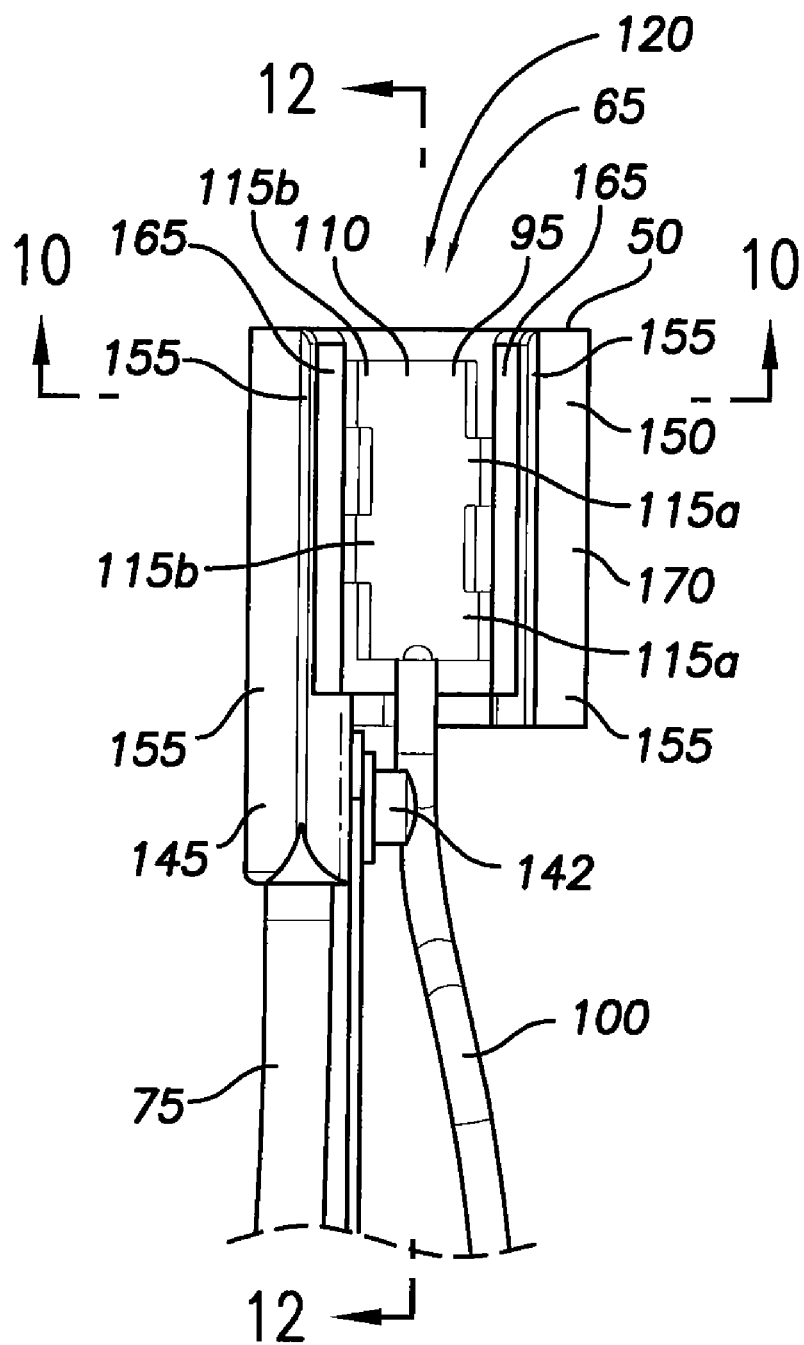
FIG. 9 is a plan view of the tray with the electrode therein, as viewed from the direction of arrow A in FIG. 2.
Figure 11:
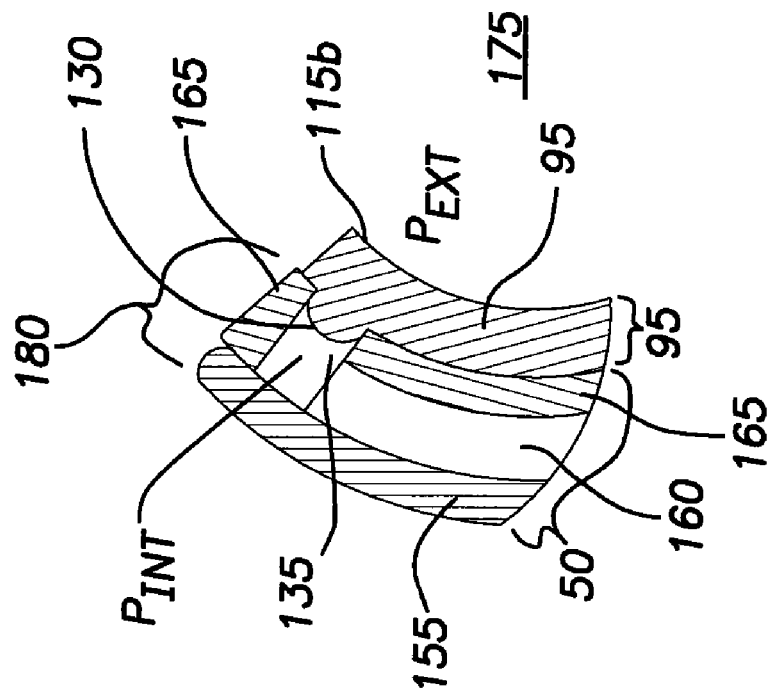
FIG. 11 is an enlarged view of a portion of the cross section depicted in FIG. 10.
Figure 10:
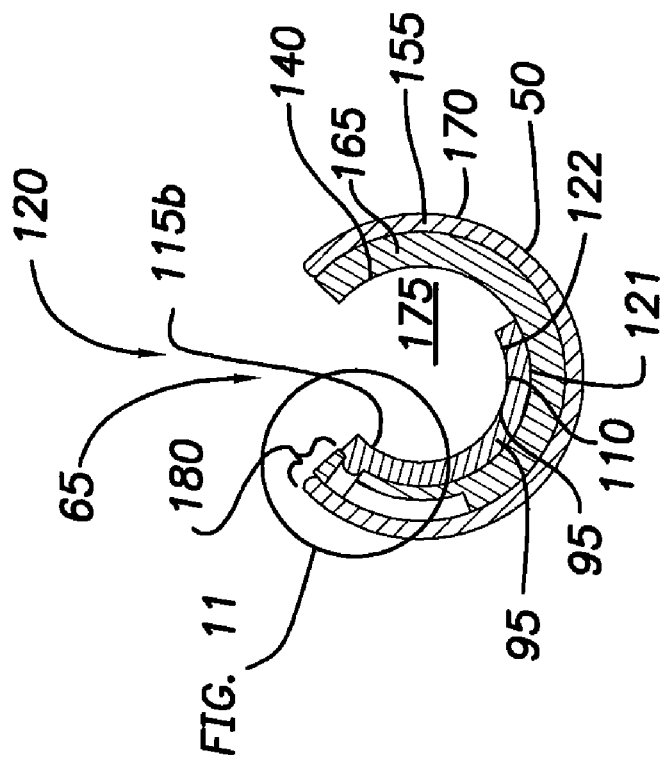
FIG. 10 is a transverse cross section through the electrode and tray, as taken along section line 10-10 in FIG. 9.
Figure 12:
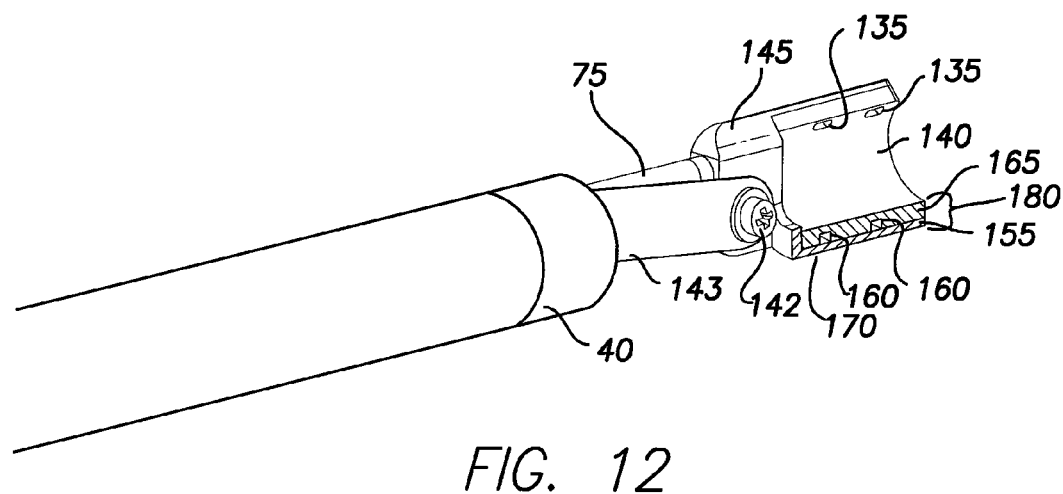
FIG. 12 is an isometric view of a longitudinal cross section of the tray without the electrode and as taken along section line 12-12 in FIG. 9.
Figure 13:
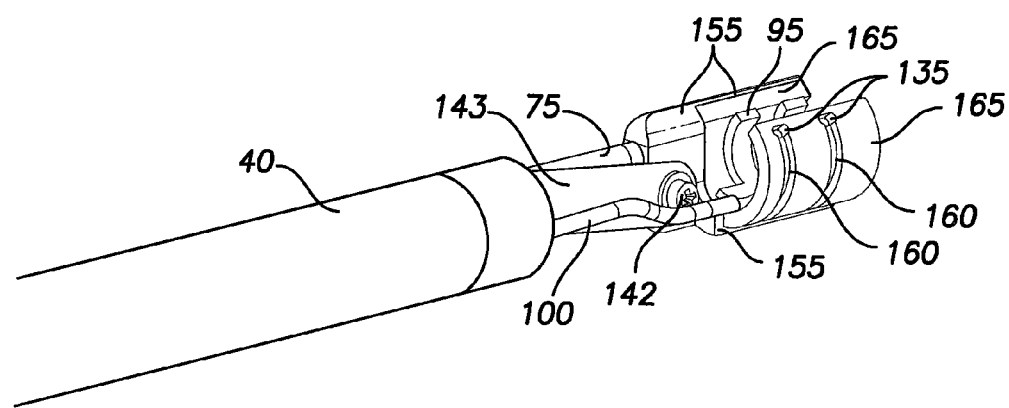
FIG. 13 is a view of the tray and electrode therein similar to that depicted in FIG. 2, except a portion of the outer jacket of the tray is removed to show the air/vacuum channels defined in the inner jacket of the tray.
Figure 14:
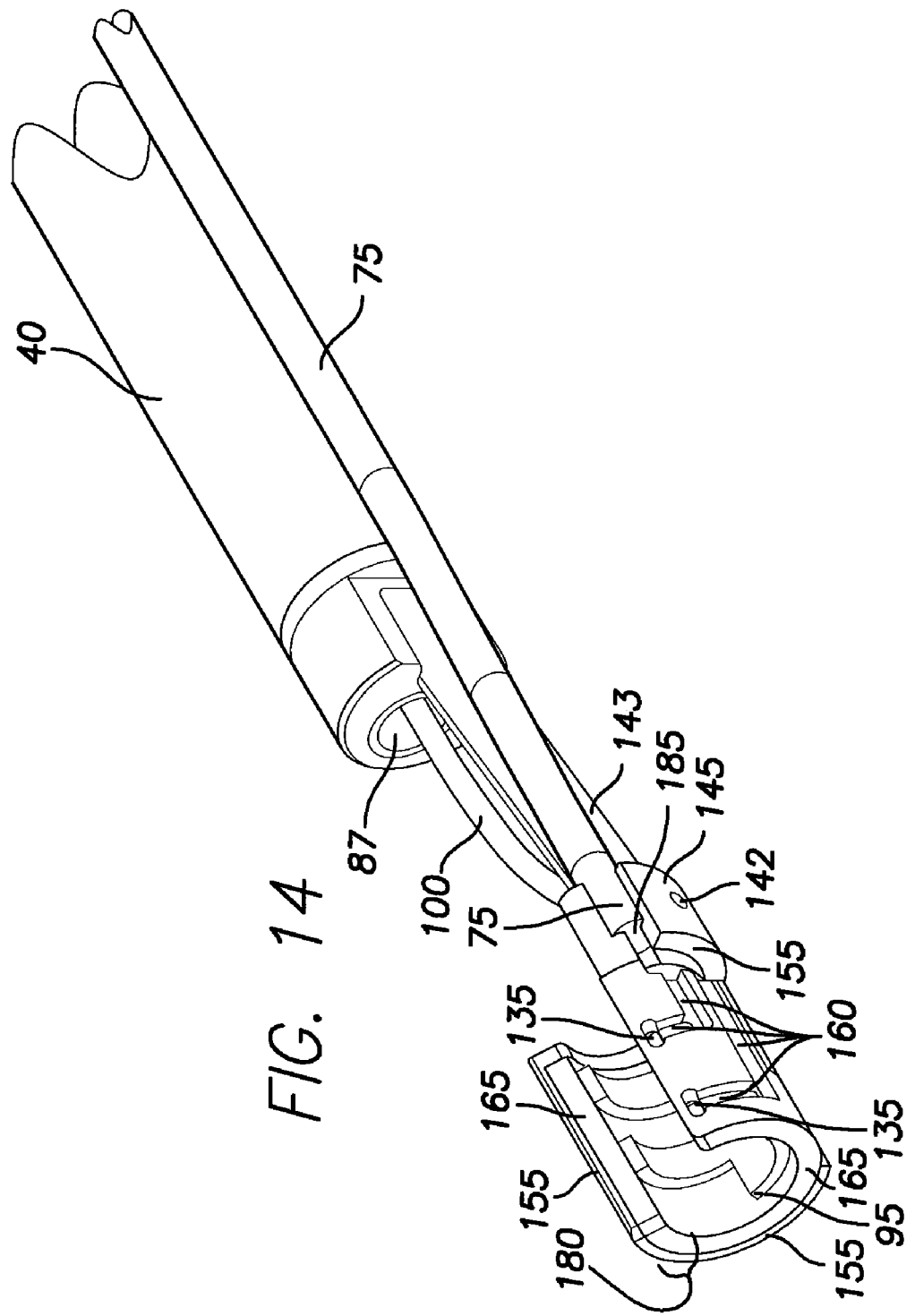
FIG. 14 is a view similar to FIG. 13, except of the opposite side of the tray.

For a discussion regarding the configuration of the electrode tray 50 and the connective relationship between the tray 50 and the lead electrode 95, reference is made to FIGS. 2 and 9-14. FIG. 9 is a plan view of the tray 50 with the electrode therein, as viewed from the direction of arrow A in FIG. 2. FIG. 10 is a transverse cross section through the electrode 95 and tray 50, as taken along section line 10-10 in FIG. 9. FIG. 11 is an enlarged view of a portion of the cross section depicted in FIG. 10. FIG. 12 is an isometric view of a longitudinal cross section of the tray 50 without the electrode 95 and as taken along section line 12-12 in FIG. 9. FIG. 13 is a view of the tray 50 and electrode 95 therein similar to that depicted in FIG. 2, except a portion of the outer jacket 155 of the tray 50 is removed to show the air/vacuum channels 160 defined in the inner jacket 165 of the tray 50. FIG. 14 is a view similar to FIG. 13, except of the opposite side of the tray 50.

As best understood from FIGS. 2, 3, 9 and 10, the electrode retention tray 50 is generally cylindrical with a cylindrical wall 180 having an outer circumferential surface 170 defining the cylindrical outer surface of the tray 50 and an inner circumferential surface 140. The inner circumferential surface 140 defines an inner cylindrical volume 175 for receiving the electrode 95 therein and provides a circumferential surface for matingly contacting the outer circumferential surface 121 of the electrode 95.

A longitudinally extending slot or gap 65 extends through the cylindrical wall 180 between the outer and inner circumferential surfaces 170, 140 of the cylindrical wall 180. As best understood from later discussed FIGS. 15 and 16, the slot 65 provides an avenue for a body structure 25 to enter an open electrode 95 held in the inner cylindrical volume 175. The slot 65 also provides an avenue for the body structure 25, with the electrode 95 closed about at least a portion of the body structure 25, to exit the volume 175.

As indicated in FIGS. 10-12, the cylindrical wall 180 includes an outer jacket or layer 155 and an inner jacket or layer 165. The exposed surface of the outer jacket 155 is the outer circumferential surface 170 of the wall 180, and the exposed surface of the inner jacket 165 is the inner circumferential surface 140 of the wall 180.

As shown in FIGS. 2, 9, 13 and 14, in one embodiment, the tray pivot arm 145 is an extension of the outer jacket 155. In other embodiments, the tray pivot arm 145 is an extension of the inner jacket 165 or an extension of both jackets 155, 165.

In one embodiment, the outer jacket 155 is made of Ultem, polycarbonate, a rigid, biocompatible polymer, etc., and the inner jacket 165 is made of Ultem, polycarbonate, a rigid, biocompatible polymer, etc. In one embodiment, the inner jacket 165 is molded or otherwise formed via a molding and/or machining process and then the outer jacket 155 is formed about the inner jacket 165 via a molding and/or machining process.

As can be understood from FIGS. 9 and 10, in one embodiment, the inner cylindrical volume 175 has a diameter of between approximately 1 mm and approximately 8 mm. In one embodiment, the inner cylindrical volume 175 has a longitudinally extending length of between approximately 2 mm and approximately 20 mm. In one embodiment, the cylindrical wall 180 has a radial thickness of between approximately 0.5 mm and approximately 4 mm. In one embodiment, the gap 65 has a circumferentially extending width of between approximately 1 mm and approximately 9 mm.

As indicated in FIGS. 10-14, air/vacuum ports 135 are defined in the inner jacket 165 and inner circumferential surface 135. Air/vacuum channels 160 are defined in the inner jacket 165. The outer jacket 155 extends over the channels 160 as the outer jacket 155 extends over the outer circumferential surface of the inner jacket 165, thereby capping/covering the channels 160 to form sealed air/vacuum conveying pathways defined in the interior of the cylindrical wall 180 of the tray 50.

As shown in FIG. 14, the channels 160 are in a manifold configuration. The channels 160 lead to the air/vacuum ports 135 from the distal lumen opening 185 in the air/vacuum line 75, thereby placing the air/vacuum ports 135 in the fluid communication with the air/vacuum source coupled to the luer 70 at the proximal end of the air/vacuum line 45 (see FIG. 1).

As indicated in FIGS. 12-14, in one embodiment, a pair of air/vacuum ports 135 is defined in the inner circumferential surface 140 near each longitudinally extending edge of the gap 65. In other embodiments, there will be a greater or lesser number of ports 135 and/or the ports will be defined in other regions of the inner circumferential surface 140.

As indicated in FIGS. 10 and 11, when the electrode 95 is held in the open configuration by the tray 50, the outer circumferential surface 121 of the electrode 95 circumferentially abuts against the inner circumferential surface 140 of the tray 50 and the protrusions 130 are received in the air/vacuum ports 135. The gaps 65, 120 of the tray 50 and electrode 95 are aligned to allow the passage of a body structure 25 into the space within the electrode 95 defined by the inner circumferential surface 122.

In one embodiment, protrusions 130 are held in the ports 135 via a friction or interference fit resulting between protrusions 130 and ports 135. In such an embodiment, as can be understood from FIGS. 11 and 14, the protrusions 130 are freed from the ports 135 by providing pressurized fluid (e.g., air, nitrogen, saline, $CO_2$, etc.) through the fluid pathway 45, 75, 160 leading to the ports 135 from a fluid supply coupled to the luer 70. The application of the pressurized fluid increases the interior pressure $P_{INT}$ (i.e., the pressure in the ports 135) over the exterior pressure $P_{EXT}$ (i.e., the ambient pressure in the cylindrical volume 175 of the tray 50). The resulting force created by the pressure differential overcomes the friction or interference fit, releasing the electrode 95 to bias into its closed configuration.

In one embodiment, the outer circumferential surface 121 of the electrode 95 is maintained against the inner circumferential surface 140 of the tray 50 to maintain the electrode 95 in the open configuration by the presence of an adhesive located between the two circumferential surfaces 121, 140. In one embodiment, the adhesive is cynoacrylate or other common adhesives for medical device assembly. As with the above-described friction or interference fit embodiment, application of the pressurized fluid in the fluid pathway 45, 75, 160 creates a pressure differential resulting in a force sufficient to overcome the adhesive and allow the electrode 95 to bias into its closed configuration.

In one embodiment, mechanical graspers are located on the tray 50 and/or electrode 95 for coupling the electrode 95 to the tray 50 in the open configuration. Application of pressurized fluid in the fluid pathway 45, 75, 160 creates a pressure differential resulting in a force sufficient to overcome the mechanical graspers and allow the electrode to bias into its closed configuration.

As can be understood from FIGS. 11 and 14, in one embodiment, protrusions 130 are held in the ports 135 via a force created by a pressure differential resulting from the exterior pressure $P_{EXT}$ (i.e., the ambient pressure in the cylindrical volume 175 of the tray 50) exceeding the internal pressure $P_{INT}$ (i.e., the pressure in the ports 135). Such a pressure differential is created and maintained by placing the fluid pathway 45, 75, 160 in a vacuum condition caused by a vacuum generator coupled to the luer 70. As long as the vacuum condition is maintained in the fluid pathway 45, 75, 160, the electrode 95 is held in the open configuration in the tray 50. Upon termination of the vacuum condition, the protrusions 130 are freed from the ports 135 and the electrode 95 can bias into the closed configuration.

Figure 17:
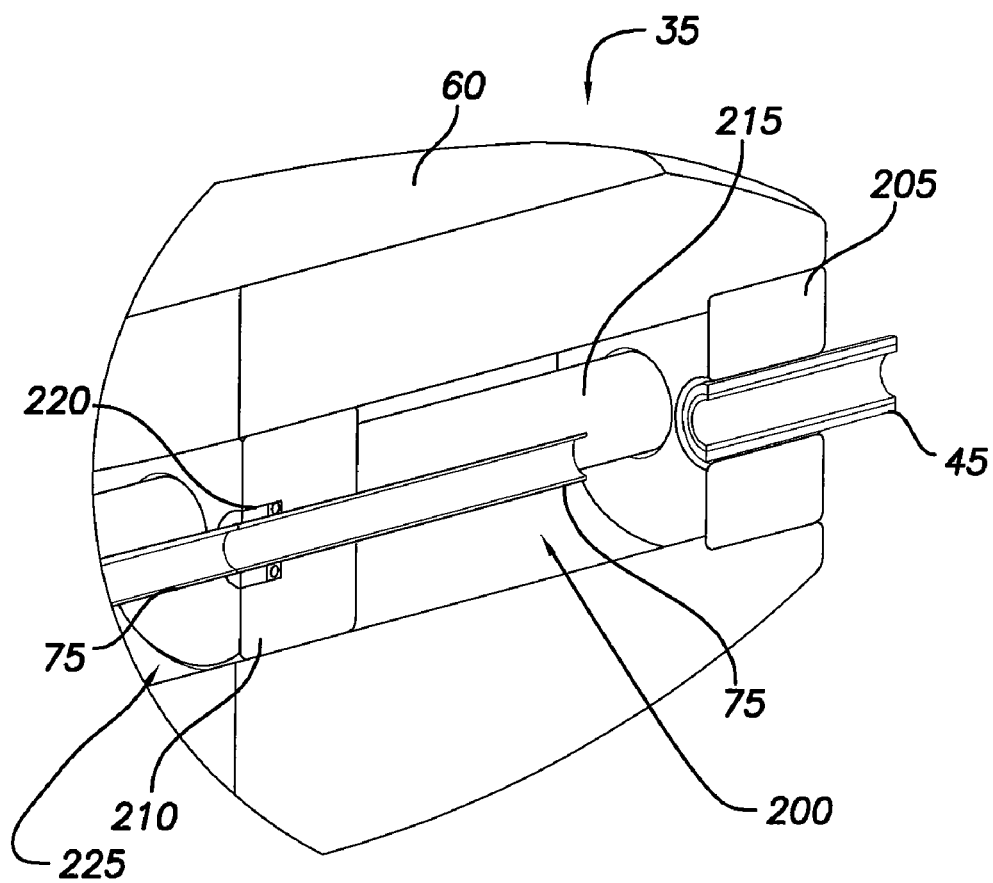
FIG. 17 is an isometric cross section view through the handle 35 as taken along section line 17-17 in FIG. 3.

As shown in FIG. 17, which is an isometric cross section view through the handle 35 as taken along section line 17-17 in FIG. 3, in one embodiment, the handle 35 has defined therein a fluid/vacuum chamber 200. The chamber 200 is a cylindrical channel generally running the length of the handle 35 between proximal and distal bulkheads 205, 210.

The proximal fluid/vacuum line 45 and the distal fluid/vacuum line 75 both open into the chamber 200. The lead receiving lumen or channel 215 extends through the chamber 200 as the lumen 215 extends between the proximal and distal ports 85, 87 of the lumen 215. However, the lead receiving lumen 215 does not open into the chamber 200.

As indicated in FIG. 17, a seal is formed between the distal bulkhead 210 and the distal fluid/vacuum line 75 by an o-ring 220. This o-ring 220 allows the distal fluid/vacuum line 75 to translate longitudinally within the distal bulkhead 210 as required to have enough play or slack in the distal line 75 to accommodate rotation of the electrode capture tray 50 relative to the shaft 40, as indicated by a comparison of FIGS. 2 and 7. To facilitate the longitudinal translation of the line 75 within the shaft 40, the line 75 extends through, and is displaceable within, a lumen 225 defined in the shaft 40 distal of the distal bulkhead 210 and extending nearly the length of the shaft 40 to daylight as the shaft opening 80 near the distal end of the shaft 40 (see FIG. 5). To prevent the line 75 from pulling through the seal 75, the line 75 extends substantially proximally into the chamber 200 before terminating.

Figure 15:
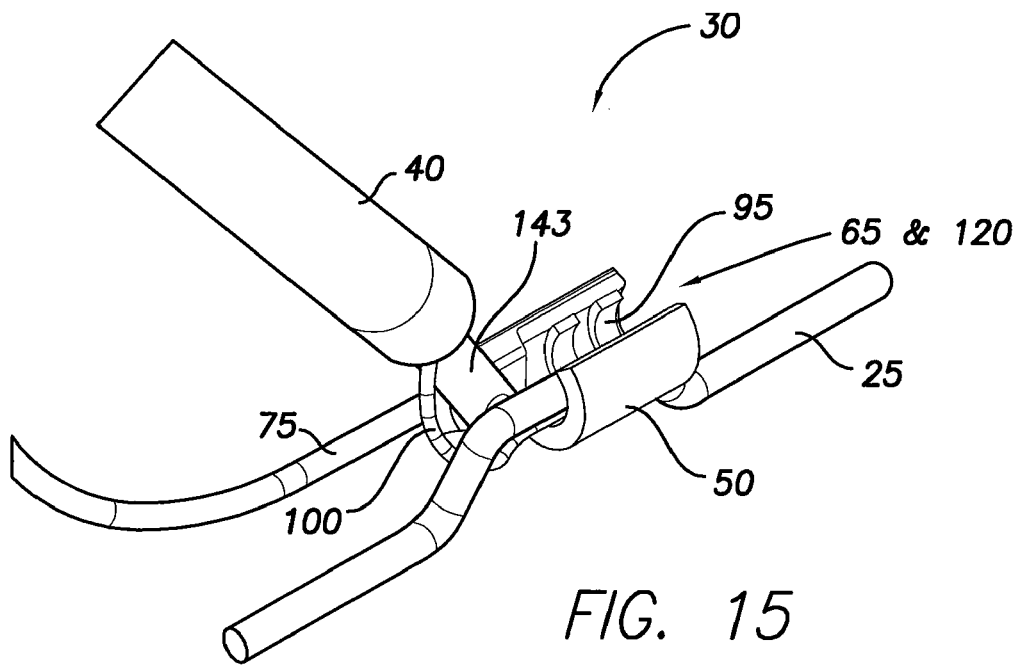
FIG. 15 is an isometric view of the tool distal end with the electrode contained within the pivoted tray, which is maintaining the electrode in the open configuration, the nerve bundle being located within the electrode.

For a discussion of a method of using the tool 10 to deploy the electrode 95 about a target structure (e.g., nerve bundle 25), reference is made to FIGS. 15 and 16. FIG. 15 is an isometric view of the tool distal end 30 with the electrode 95 contained within the pivoted tray 50, which is maintaining the electrode 25 in the open configuration, the nerve bundle 25 being located within the electrode 95 FIG. 16 is the same view depicted in FIG. 15, except the electrode 95 is engaged about the nerve bundle 25 and the electrode 95 has been released from the tray 50.

In one embodiment, the delivery tool 10 and lead 90 carried by the tool are introduced into the body via a minimally invasive procedure. For example, the tool and lead can be introduced via a percutaneous puncture via an introducer sheath. Similarly, the tool and lead can be introduced via a laparoscopic access cannula.

As can be understood from FIG. 15, the tool distal end 30, with its tray 50 articulated relative to the shaft 40, is maneuvered into position adjacent the nerve 25. The tray 50 holds the electrode in the open configuration such that the electrode 95 and tray gaps 120, 65 coincide to allow the nerve 25 to enter the electrode 95. The nerve 25 is received in the open electrode 95 to appear as depicted in FIG. 15.

As discussed above, in one embodiment, the electrode 95 is maintained in the open configuration via an adhesive between the electrode 95 and tray 50. Upon the nerve 25 being received in the open electrode 95, pressurized fluid, which is supplied to the tray 50 via the line 75, is applied against the electrode 95 to separate the electrode 95 from the tray 50. Upon separation of the electrode from the tray, the electrode is free to bias into the closed configuration, thereby enclosing the nerve 25 within the electrode 95, as depicted in FIG. 16.

As discussed above, in one embodiment, the electrode 95 is maintained in the open configuration via a friction or interference fit between the electrode 95 and tray 50. Upon the nerve 25 being received in the open electrode 95, pressurized fluid, which is supplied to the tray 50 via the line 75, is applied against the electrode 95 to separate the electrode 95 from the tray 50. Upon separation of the electrode from the tray, the electrode is free to bias into the closed configuration, thereby enclosing the nerve 25 within the electrode 95, as depicted in FIG. 16.

As discussed above, in one embodiment, the electrode 95 is maintained in the open configuration via a vacuum condition established between the electrode 95 and tray 50. The vacuum condition is transmitted from a vacuum generator to the tray 50 via the line 75. Upon the nerve 25 being received in the open electrode 95, the vacuum condition is terminated, thereby freeing the electrode 95 to separate from the tray 50. Upon separation of the electrode from the tray, the electrode is free to bias into the closed configuration, thereby enclosing the nerve 25 within the electrode 95, as depicted in FIG. 16.

In each of the three aforementioned embodiments, upon the electrode 95 attaching to the nerve 25, the tool 10 can be retracted from the electrode 95. As the tool 10 is retracted, the lead body 100 slides through the shaft 40 until the lead distal end exits the shaft 40. The lead connective end 105 can then be electrically coupled to a pulse generator or other energy source.

Although the present invention has been described with reference to preferred embodiments, persons skilled in the art will recognize that changes may be made in form and detail without departing from the spirit and scope of the invention.

What is claimed is:

1. A tool for delivering an implantable electrode about a nerve or nerve bundle of a patient, the implantable electrode including a generally cylindrical body having a gap defined therein, the tool comprising:
    a shaft defining a proximal end and a distal end; and
    an electrode tray articulatably coupled to the distal end and configured to maintain the electrode in an open configuration until the electrode is delivered about the nerve or nerve bundle;
    wherein the tray is generally cylindrical in shape and extends longitudinally from a proximal end to a distal end, wherein a slot longitudinally extends through an entire side of the tray from the distal end to the proximal end, and wherein the electrode gap and the tray slot align to allow the nerve or nerve bundle to enter the electrode and tray slot when the electrode is held in an open configuration within the tray and to allow the nerve or nerve bundle to exit the electrode and tray slot when the electrode is held in an open configuration; and
    wherein the tray is articulatably coupled to the distal end via a pivot axis, the pivot axis being substantially perpendicular to a longitudinal axis of the shaft.

2. The tool of claim 1, further comprising a friction or interference fit between a feature of the electrode and a feature of the tray to maintain the electrode in an open configuration.

3. The tool of claim 1, further comprising a mechanical arrangement between the electrode and tray adapted to maintain the electrode in an open configuration.

4. The tool of claim 1, further comprising an adhesive between the electrode and tray adapted to maintain the electrode in an open configuration.

5. The tool of claim 1, further comprising a vacuum condition existing between the electrode and tray adapted to maintain the electrode in an open configuration.

6. The tool of claim 1, further comprising a fluid or vacuum pathway extending from the distal end to the tray.

7. The tool of claim 1, wherein longitudinal displacement within the shaft of a lead body extending from the electrode causes the tray to articulate relative to the shaft when the electrode is located within the tray.

8. A medical system for administering electrotherapy to a nerve or nerve bundle, the system comprising: a lead including a longitudinally extending body and an electrode coupled to a distal end of the body, the electrode including a generally cylindrical body having a gap defined therein when the electrode is in an open configuration; and a tool for delivering the electrode about the body and including a shaft and a tray articulatably coupled to a distal end of the shaft, wherein the tray is generally cylindrical and extends longitudinally from a proximal end to a distal end, and wherein a slot longitudinally extends through an entire side of the tray from the distal end to the proximal end, wherein the electrode gap and tray slot align to allow the nerve or nerve bundle to enter the electrode when the electrode is held in an open configuration within the tray, wherein the tray is articulatably coupled to the distal end via a pivot axis, and wherein the pivot axis is substantially perpendicular to a longitudinal axis of the shaft.

9. The system of claim 8, wherein the electrode is maintained in the open configuration by an adhesive between the electrode and tray.

10. The system of claim 8, wherein the electrode is maintained in the open configuration by an interference or friction fit between features of the electrode and features of the tray.

11. The system of claim 8, wherein the electrode is maintained in the open configuration by maintaining a vacuum state between the electrode and tray.

* * * * *